United States Patent [19]

Rusek et al.

[11] Patent Number: 4,833,255
[45] Date of Patent: May 23, 1989

[54] PROCESS FOR THE PREPARATION OF INDOLINE

[75] Inventors: Milos Rusek, Binningen; Hermann Kny, Füllinsdorf, both of Switzerland

[73] Assignee: Ciba-Geigy Corporation, Ardsley, N.Y.

[21] Appl. No.: 71,436

[22] Filed: Jul. 9, 1987

Related U.S. Application Data

[63] Continuation-in-part of Ser. No. 813,818, Dec. 27, 1985, abandoned, which is a continuation-in-part of Ser. No. 610,727, May 16, 1984, abandoned.

[51] Int. Cl.$^4$ ............................................. C07D 209/08
[52] U.S. Cl. ................................................... 548/490
[58] Field of Search ........................................ 548/490

[56] References Cited

U.S. PATENT DOCUMENTS 4,474,969  10/1984  Honda et al. ..................... 548/508

FOREIGN PATENT DOCUMENTS

| 606027 | 11/1934 | Fed. Rep. of Germany . |
| 2328330 | 12/1974 | Fed. Rep. of Germany . |
| 52-108969 | 9/1977 | Japan . |
| 58-146562 | 9/1983 | Japan . |
| 58-146563 | 9/1983 | Japan . |
| 1394374 | 5/1972 | United Kingdom . |
| 1394373 | 5/1972 | United Kingdom . |
| 2051065 | 5/1980 | United Kingdom . |

OTHER PUBLICATIONS

Kh. Minachev, Chem. Abstracts, vol. 81, No. 168887r, (1974), Catalytic Activity of Rare Earth Oxides.
H. Bremer et al., Chem. Abstracts, vol. 75, No. 80699w, (1971), Relation Among Surface-Chemical, Structural and Catalytic Properties of Roasted Magnesium Oxide-Silicon Dioxide Catalysts.
J. Bakke et al., Acta Chem. Scand. B28, (1974), 393-398.
Linde Molecular Sieves, Catalyst Bulletin, Union Carbride, N.Y.
Bull. Soc. Chim Fr. 1931, 49, 3-7.
Chemical Abstracts, vol. 88, No. 104880(1978).
S. Bernal et al., J. Catalysis 66, 184-190(1980).
Advanced Inorganic Chemistry, F. Albert Cotton et al., pp. 386-392.
Abstract of Japanese Kokai No. 52-108969, Dec. 9, 1977.

Primary Examiner—Mary E. Ceperley
Attorney, Agent, or Firm—Kevin T. Mansfield; Edward McC. Roberts

[57] ABSTRACT

A process for the preparation of indoline without substantial formation of indole, comprises passing 2-(2-aminophenyl)ethanol, in a vapor phase and admixed with a carrier gas, at a temperature of from about 240° to about 260° C. over at least a catalytic amount of a metal silicate or aluminosilicate containing alkaline earth metal or rare earth metal ions. The carrier gas can be water in the form of steam. The passage of 2-(2-aminophenyl)ethanol over the catalyst can be periodically terminated and the catalyst reactivatd by passing a mixture of air and nitrogen over the catalyst at a temperature of from about 300° to about 550° C., after which the passage of 2-(2-aminophenyl)ethanol and carrier gas can be resumed.

7 Claims, No Drawings

PROCESS FOR THE PREPARATION OF INDOLINE

CROSS REFERENCE TO RELATED APPLICATIONS

This is a continuation-in-part of Ser. No. 813,818, filed Dec. 27, 1985, now abandoned, which in turn is a continuation-in-part of Ser. No. 610,727, filed May 16, 1984, now abandoned.

FIELD OF INVENTION

The present invention pertains to a catalytic process for the preparation of indoline from 2-(2-aminophenyl)ethanol without substantial formation of indole and with a readily reactivated catalyst.

BRIEF DESCRIPTION OF PRIOR ART

Indoline is an intermediate for various compounds including the bactericidal and fungicidal pyrrolo[3.2.1-i,j]quinolines of British Patent Specification Nos. 1,394,373 and 1,394,374.

German Patent Specification No. 606,027 discloses the preparation of indoline from 2-(2-aminophenyl)ethanol using condensing agents such as oxides of aluminum, titanium, zirconium, chromium, and thorium. These condensing agents are rapidly deactivated and moreover the reaction is generally non-selective, producing both indoline and indole.

Bakke et al., Acta Chem. Scand., 28 (1974) 393–398 describe the formation of indoline from 2-(2-aminophenyl)-ethanol using silica gel but this catalyst has a short life under industrial conditions and also is non-selective.

Japanese Patent Disclosure No. Sho 52-108969 reports on the formation of indoline from 2-(2-aminophenyl)ethanol by heating the latter in the liquid phase without the use of a catalyst. Under these conditions the reaction is unselective and of a low reaction rate.

Japanese Patent Disclosure No. Sho 58-146562 reports on the formation of indoline from 2-(2-aminophenyl)ethanol in the vapor phase utilizing boric acid or phosphoric acid supported on granular alumina or silica gel. These catalysts are short lived and, since they appear to entrap the water which is a reaction product (none exiting with the product), their regeneration is complicated.

Japanese Patent Disclosure No. Sho 58-146563 reports on the formation of indoline from 2-(2-aminophenyl)ethanol by heating the latter in the liquid phase with phosphoric acid, an alumina-based solid acid catalyst, or a titanium-based solid acid catalyst. Use of these catalysts in the liquid phase reaction produced yields ranging from about 85 to 97.7% whereas the use of magnesium oxide and silicon dioxide produced a yield of 57.3%.

DETAILED DESCRIPTION

The present invention involves the improvement in the formation of indoline from 2-(2-aminophenyl)ethanol in which the 2-(2-aminophenyl)ethanol is passed, in a vapor phase and admixed with a carrier gas, and at a temperature of from about 240° to about 260° C., over a catalyst consisting of a metal silicate or aluminosilicate which, however, contains alkaline earth metal or rare earth metal ions. The selectivity and yield of the reaction under these conditions is excellent and the catalyst not only has a long life with constant activity but can be readily and inexpensively regenerated.

The process can be carried out under reduced pressures but preferably is conducted at normal atmospheric pressures. The carrier can be an inert gas such as hydrogen, nitrogen, carbon dioxide, or water in the form of steam. Preferably the carrier gas is steam which is supplied in a quantity to provide from 0.2 to 10 moles of water per mole of 2-(2-aminophenyl)ethanol and particularly 3 to 5 moles of water per mole of 2-(2-aminophenyl)ethanol. While water is formed in the reaction, the addition or use of water as the carrier surprisingly has been found to be advantageous in terms of catalyst life.

The catalysts, namely the metal silicates or aluminosilicates containing alkaline earth metal or rare earth metal ions, are commercially available or can be readily prepared. Thus an aqueous solution of an alkali metal silicate such as potassium silicate can be allowed to react with an alkaline earth metal salt such as magnesium nitrate. The resulting alkaline earth metal silicate, as for example non-stoichiometric magnesium silicate, is collected by filtration, washed, and dried, and then activated by the passage of air over the material at a temperature of 300° to 350° C.

In addition, a metal silicate or aluminosilicate molecular sieve containing alkaline earth metal or rare earth metal ions, such as those sold as "Linde Molecular Sieves" by Union Carbide or those of Strem (such as Strem 14-8910 containing approximately 11% rare earth metal ions, reported as their oxides) can be employed.

Although the life of the catalyst is surprising longer than those heretofore employed, the catalyst will require periodic reactivation. This can be readily done by terminating the passage of the 2-(2-aminophenyl)ethanol over the catalyst, simply passing a mixture of air and nitrogen over the catalyst at a temperature of from about 300° to about 550° C. until it is reactivated, and thereafter resuming the passage of 2-(2-aminophenyl)ethanol according to the method already described.

Indoline is formed in the present process without the formation of substantial amounts of indole and with a selectivity of over 97%. Conversion rates over 98% are consistently observed.

The following examples will serve to further illustrate the nature of the invention but should not be construed as a limitation on the scope thereof which is defined sole by the appended claims.

EXAMPLE 1

A solution of 400 g of magnesium nitrate hexahydrate in 6 L of water is stirred with a solution of 720 ml of potassium silicate in 6 L of water (9.6% Si; $d = 1.262_{20°\,C.}$). The solid is collected by filtration, washed with water, dried, and heated at 350° C. for 5 hours.

A 65% aqueous solution of 2-(2-aminophenyl)ethanol is passed over 3 ml of the foregoing catalyst heated to 260° C. in a microreactor at a rate of 3 ml/h. The exit gas is analyzed by gas chromatography.

Over a four day experiment using these conditions, the following results were consistently registered:

Conversion: 98.1–99.9%

Selectivity (based on reacted 2-(2-aminophenyl)ethanol):
  95.3–98.3%.

EXAMPLE 2

A base reactor is charged with 100 ml of "10X" molecular sieve (Union Carbide) and heated to 250° C. at a rate of 100° C./h. A 65% aqueous solution of 2-(2-aminophenyl)ethanol containing 5% hydrocarbons as impurities then is introduced at a rate of 68.5 g (0.5 mole/h) at atmospheric pressure, maintaining the temperature at 250° C.

The following average results were observed over a 24 hour period:
Conversion: 99%
Selectivity (based on reacted 2-(2-aminophenyl)ethanol): 97%.

EXAMPLE 3

A microreactor is charged with 2.45 ml of Strem Chem. molecular sieve 14-8910 (an aluminosilicate molecular sieve containing 10.7% rare earth metal oxides). The reactor is heated to 250° C. at a rate of 100° C./h and then held at 240° C. while a 65% aquous solution of 2-(2-aminophenyl)ethanol is introduced at atmospheric pressure at a rate of 3 ml/h.

The following average results were observed over an 8 hour period:
Conversion: 99%
Selectivity (based on reacted 2-(2-aminophenyl)ethanol): 98%.

What is claimed is:

1. In the process for the preparation of indoline from 2-(2-aminophenyl)ethanol without substantial formation of indole, the improvement which comprises passing said 2-(2-aminophenyl)ethanol, in a vapor phase and admixed with a carrier gas, at a temperature of from about 240° to about 260° C. over a catalytic amount of a metal silicate or aluminosilicate containing alkaline earth metal or rare earth metal ions.

2. The process according to claim 1 wherein the reaction is conducted at normal atmospheric pressures.

3. The process according to claim 1 wherein said carrier gas comprises from 0.2 to 10 moles of water per mole of 2-(2-aminophenyl)ethanol.

4. The process according to claim 3 wherein said carrier gas comprises from 3 to 5 moles of water per mole of 2-(2-aminophenyl)ethanol.

5. The process according to claim 1 wherein said metal silicate or aluminosilicate containing alkaline earth metal or rare earth metal ions is magnesium silicate.

6. The process according to claim 1 wherein said metal silicate or aluminosilicate containing alkaline earth metal or rare earth metal ions is a molecular sieve containing said alkaline earth metal or rare earth metal ions.

7. The process according to claim 1 including the steps of periodically terminating the passage of said 2-(2-aminophenyl)ethanol over the metal silicate or aluminosilicate containing alkaline earth metal or rare earth metal ions, passing a mixture of air and nitrogen at a temperature of from about 300° to about 550° C. over the metal silicate or aluminosilicate containing alkaline earth metal or rare earth metal ions to activate the same, and thereafter resuming the passage of said 2-(2-aminophenyl)ethanol.

* * * * *